US00PP21738P3

(12) United States Plant Patent
Lee

(10) Patent No.: US PP21,738 P3
(45) Date of Patent: Mar. 1, 2011

(54) ***LOROPETALUM CHINENSE* PLANT NAMED 'SHANG-WHITE'**

(50) Latin Name: *Loropetalum chinense*
Varietal Denomination: Shang-white

(75) Inventor: Robert Edward Lee, Independence, LA (US)

(73) Assignees: Robert Edward Lee, Independence, LA (US); Plant Development Services, Inc., Loxley, AL (US)

( * ) Notice: Subject to any disclaimer, the term of this patent is extended or adjusted under 35 U.S.C. 154(b) by 0 days.

(21) Appl. No.: 12/458,474

(22) Filed: Jul. 14, 2009

(65) Prior Publication Data

US 2011/0016593 P1 Jan. 20, 2011

(51) Int. Cl.
*A01H 5/00* (2006.01)

(52) U.S. Cl. ..... Plt./226

(58) Field of Classification Search ..... Plt./226

See application file for complete search history.

*Primary Examiner*—Susan B McCormick Ewoldt
(74) *Attorney, Agent, or Firm*—Breiner & Breiner, LLC

(57) ABSTRACT

A new and distinct variety of *Loropetalum chinense* plant named 'Shang-white' characterized by its dense, globose growth habit, dark green foliage color, and abundance of white flowers is disclosed.

1 Drawing Sheet

Genus species: *Loropetalum chinense.*
Varietal denomination: 'Shang-white'.

FIELD OF INVENTION

The present invention relates to a new and distinct variety of the genus *Loropetalum* and a member of the Hamamelidaceae family. This new *Loropetalum* variety, hereinafter referred to as 'Shang-white', was discovered by Robert Edward Lee in April, 1998. 'Shang-white' is characterized by its dense, globose growth habit, dark green foliage color, and abundance of white flowers.

BACKGROUND OF THE INVENTION

'Shang-white' was found as an openly pollinated seedling in a group of unnamed, unpatented *Loropetalum chinense* plants being grown in a nursery in Independence, La. The value of this new cultivar lies in its dense, globose growth habit, dark green foliage color, and abundance of white flowers. 'Shang-white' has retained many of the outstanding attributes of its parent variety, in particular its tolerance of heat and disease, which makes it adaptable to culture in most of the Sunbelt States. As with the parent species, the plant of this invention may be advantageously employed as a specimen appointment, in either formal or informal groupings, and is quite attractive in mass plantings. 'Shang-white' serves well in foundation plantings and is adaptable for culture as a potted plant. 'Shang-white' is responsive to pruning and training and may be employed in forming dense, attractive hedges, and maintained without an excessive amount of care. This plant is easy to care for and maintain in size due to its short internodes, heavy branching, and dense canopy. Its natural propensity to remain small to maturity makes it valuable for landscape uses in smaller home gardens which require plants that do not outgrow their intended mature dimensions.

Asexual propagation of the new plant by cuttings has been under Mr. Lee's direction and control in Independence, La. The new plant retains its distinctive characteristics and reproduces true to type in successive generations of asexual reproduction. The plant cannot be reproduced true from seed.

SUMMARY OF THE INVENTION

The following are the most outstanding and distinguishing characteristics of this new cultivar when grown under normal horticultural practices in Independence, La.

1. Dense and globose in nature.
2. The upper surface of the mature leaf is a lustrous dark green color.
3. Fast growth rate under normal fertilization and moisture conditions.
4. Hardy to Zone 7.
5. Tolerates full sun to part shade.
6. Heat tolerant.
7. Easily propagated with semi-hardwood cuttings in late spring through the summer.
8. Requires little pruning but is tolerant if pruning is needed.
9. Relatively pest resistant.
10. Good specimen plant.
11. Good foundation plant.
12. Makes a very good, dense hedge.
13. Very desirable in planters.
14. The flowers are white and profuse.

DESCRIPTION OF THE DRAWINGS

This new *Loropetalum chinense* cultivar is illustrated by the accompanying photographic prints in which.

Figure 1:
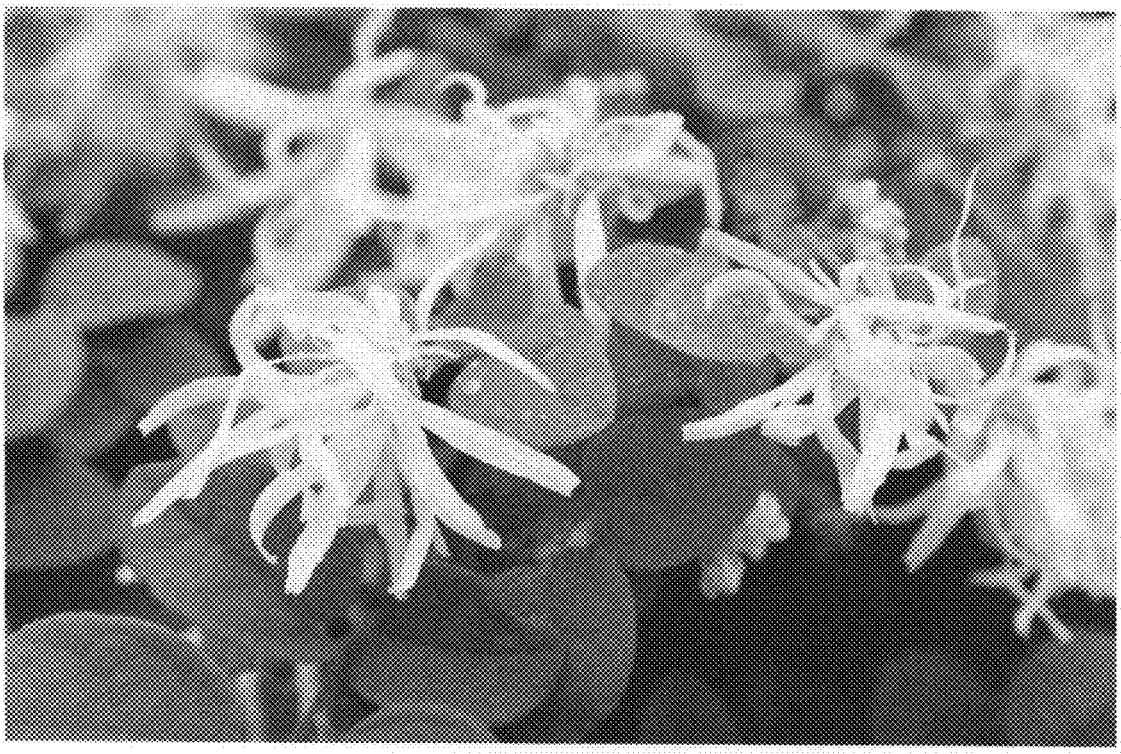
FIG. 1 is a photograph of a close-up showing the flower, buds, foliage and stem color, as well as flower size and form of the new *Loropetalum chinese* cultivar of the present invention.
Figure 2:
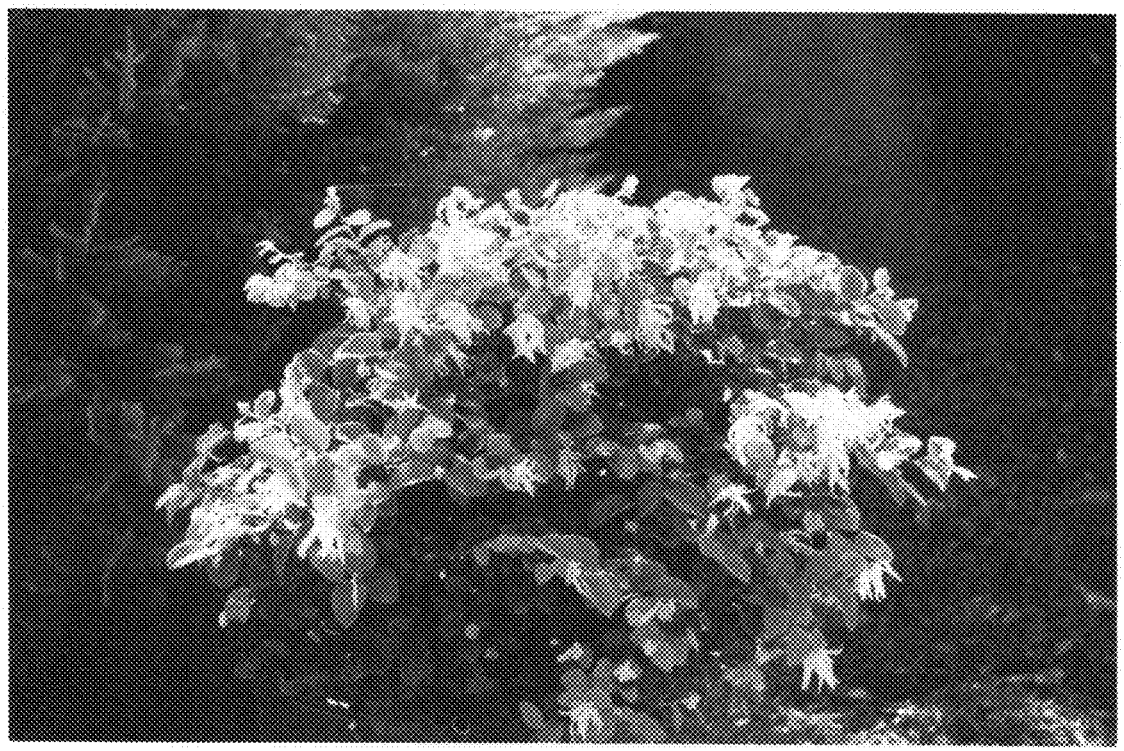
FIG. 2 is a photograph showing the dense and globose growth habit of a three gallon plant of the new *Loropetalum chinese* cultivar of the present invention.

The colors shown are as true as is reasonably possible to obtain by conventional photographic procedures. Colors in the photographs may appear different than actual colors due to light reflectance. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of *Loropetalum* based on observations made of two year old plants grown in three gallon containers in commercial production practices, in greenhouses, and in established landscape plantings in Independence, La. and including a comparison with *Loropetalum chinense* (unpatented parent) and *Loropetalum chinense* 'NCI002' U.S. Plant Pat. No. 18,977.

DISTINCTIVE CHARACTERISTICS

TABLE 1

| Characteristic | *Loropetalum c.* 'Shang-white' | (unpatented parent) *Loropetalum chinense* | *Loropetalum c.* 'NCI002' U.S. Plant Pat. No. 18,977 |
|---|---|---|---|
| Height (Mature) | 3-4' (0.9-1.2 m) | 10-12' (3.0-3.7 m) | 18" (44.7 cm) |
| Width (Mature) | 3-4' (0.9-1.2 m) | 8-9' (2.4-2.7 m) | 33" (83.8 cm) |
| Leaf Length | 1 1/16-1 1/2" (2.66-3.8 cm) | 1-2 1/2" (2.5-6.3 cm) | 15/16" (2.4 cm) |
| Leaf Width | 3/4-1 1/8" (1.9-2.9 cm) | 3/4-1 1/4" (1.9-3.1 cm) | 9/16" (1.4 cm) |
| Growth Habit | Dense, Globose | Upright, Spreading | Dense, Broad-rounded |
| Foliage Color (Imature) | Yellow-Green G. 144A | Yellow-Green G. 146C | Greyed-Orange G. 176B turning to Yellow-Green G. 146B |
| Flower Color | White G. 155A | White G. 155A | White G. 155C |
| Leaf Shape | Ovate-rounded | Ovate-rounded | Ovate |

The female, or seed parent, of 'Shang-white' is *Loropetalum chinense* (unpatented) which is a native of China. *Loropetalum chinense* was first introduced to Europe in the 1880's and is believed to have been cultivated in North America since the early 1930's.

*Loropetalum chinense* and *Loropetalum chinense* 'NCI002' U.S. Plant Pat. No. 18,997 are well known in the industry and are comparable to 'Shang-white' in that all have green foliage color and white blooms. However, there are many differences. The growth habit of 'Shang-white' is dense and globose to 4' (1.2 m) tall compared to the parent variety which is a much taller grower with an upright spreading habit. The cultivar 'NCI002' has a shorter, more broad growth habit than 'Shang-white'. In addition, the new growth of 'NCI002' has a greyed-orange tint which is not characteristic of 'Shang-white'.

CLASSIFICATION

Botanical: *Loropetalum chinense* 'Shang-white'.

Parentage: Openly pollinated, unnamed, unpatented seedling of *Loropetalum chinense.*

Commercial: Broadleaf evergreen.

Form: Dense and globose.

Height: 3-4' (0.9-1.2 m).

Width: 3-4' (0.9-1.2 m).

Growth rate: Fast under normal fertilization and moisture conditions. Semi-hardwood cuttings taken in late spring and through the summer produce rooted cuttings in four to five months in Independence, La. Root development is vigorous and finely branched. In a period of four years from a rooted cutting, the plant reaches a height of 2 feet (61 cm) and a spread of 2 feet (61 cm) under normal growing conditions in Independence, La. The plant normally grows at the rate of about 8 inches (20 cm) or more per year and reaches a height of 4 feet (1.2 m) and a spread of 4 feet (1.2 m) at maturity while maintaining a dense habit due to the abundant branch development.

Foliage: Alternate, simple, evergreen, ovate-rounded, sparsely stellate-pubescent, coriaceous, almost flat, and varying in size from 1/16" (2.7 cm) to 1 1/2" (3.8 cm) long and 3/4" (1.9 cm) to 1 1/8" (2.9 cm) wide. The petioles are 1/8" (0.3 cm) to 3/16" (0.5 cm) long, 1/32" (0.08 cm) in diameter, heavily stellate-pubescent and Yellow-Green Group 146B. The venation pattern is pinnate. The base of the leaf is oblique, the margin entire, and the apex acute. The upper surface of the immature leaf is Yellow-Green Group 144A and the underside is Yellow-Green Group 146D. Immature midribs and veins are depressed on the upper side (Yellow-Green Group 144B) and prominent on the underside (Yellow-Green Group 146D). These immature leaf colors last three to four weeks in Independence, La. The upper surface of the mature leaf is Green Group 139A and the underside is Yellow-Green Group 146B. Mature midribs and veins are depressed on the upper side (Green Group 139A) and prominent on the under side (Yellow-Green Group 146D). These mature leaf colors are persistent throughout the winter. The paired foliaceous stipules are 1/8" (0.3 cm) to 3/16" (0.5 cm) long and 1/32" (0.08 cm) to 1/16" (0.16 cm) wide. The upper surface and under surface are Yellow-Green Group 144A. The stipules are caducous.

In 2008, the date of initial spring growth was March 12, in Independence, La. After the initial spring flush there was almost continuous slow growth until fall, ending October 30, also in Independence, La. When grown in full sun, the internode length of this plant is 1/4" (0.6 cm) to 1/2" (1.3 cm). When grown in light shade the internode length is 3/8" (0.9 cm) to 3/4" (1.9 cm). As would be expected, a plant grown in the shade results in a taller, less dense plant with larger leaves.

Stems, branches and trunk: The young stems are Greyed-Purple Group 183C and heavily stellate-pubescent. As the stems mature they become Yellow-Green Group 146D and by the second growing season they mature to Brown Group 200C and this color persists through the life of the plant. Also, the branches and the trunk are glabrous and rugose. In the second growing season, the stems average about 8" (20.3 cm) or more in length and about 1/16" (0.2 cm) in diameter. Also in the second growing season, the branches average about 8" (20.3 cm) or more in length and about 1/8" (0.3 cm) in diameter. In the third growing season, the trunk is about 5/8" (1.6 cm) to 3/4" (1.9 cm) in diameter at about 6" (15.2 cm) above the soil. The pith is solid and uniform. Young and older stems are densely branched.

Flowers: Perfect, White Group 155A (upper surface and under surface), glabrous, four strap-shaped petals. The flowers form a loose funnel, are borne on current season's growth, and are non-fragrant; they last on the plant in the garden five to seven days. Tight buds at 3/16" (0.5 cm) are orbicular, Green-Yellow Group 1C and pubescent. Six to eight flowers form globose heads on branchlet terminals and occasionally one to two flowers in the leaf axils. Flowering occurs from early March to late March with light repeat blooming throughout the growing season. These racemes are 1¼" (3.1 cm) to 1⅝" (4.1 cm) in diameter by ⅝" (1.6 cm) to 1" (2.5 cm) in depth and abundantly cover the plant. The flowers are attached in a circular pattern to short peduncles which are pubescent, 1/16" (0.2 cm) long, 1/32" (0.08 cm) in diameter and Yellow-Green Group 146D. The four petals which arise from the calyx tube at the sepal base are linear, crinkled, ⅝" (1.6 cm) to 1" (2.5 cm) long, 1/16" (0.2 cm) to ⅛" (0.3 cm) wide, with retuse apexes and entire margins. There are four stamens 1/32" (0.08 cm) long, Green-Yellow Group 1D, with anthers also Green-Yellow Group 1D. Pollen matures to Yellow-Green Group 11C and is produced in very small amounts. The two pistils are 1/32" (0.08 cm) long and Green-Yellow Group 1D. The ovary is inferior and two-celled. Each flower has four sepals that have entire revolute margins which are 1/16" (0.2 cm) long, 1/16" (0.2 cm) wide, ovate, and fused into a calyx. The calyx is 3/16" (0.5 cm) in diameter, 3/16" (0.5 cm) in depth, pubescent and Yellow-Green Group 145C outer surface and Yellow-Green Group 145B inner surface.

Fruit: Woody, scabrous, ovoid, 3/16" (0.5 cm) to 5/16" (0.8 cm) long, ⅛" (0.3 cm) to ¼" (0.6 cm) in diameter, two-celled capsule, one seed per cell. Mature plants produce 100 to 125 fruits which are Yellow-Green Group 146B. Seeds are ⅛" (0.3 cm) to 3/16" (0.5 cm) long, 1/16" (0.2 cm) to ⅛" (0.3 cm) in diameter, Brown Group 200C, and mature in the fall.

Culture: Grows well in a wide range of conditions and tolerates sun to part shade. Prefers a moist, well-drained soil that is rich in organic matter. Responds well to mulching and medium applications of fertilizer; prefers pH 6 to 7. Very little pruning is needed. Adaptable to containers and above ground planters. Makes a good foundation plant or informal hedge with excellent foliage and flower contrast. Ideal for coastal regions and warmer parts of the Piedmont. Cold hardiness and drought resistance are comparable to the parent variety. Propagated with semi-hardwood cuttings in late spring through the summer.

Disease and insect resistance: Resistance to disease and insects common to plants of Loropetalum has not been observed.

The exemplary embodiments herein disclosed are not intended to be exhaustive or to unnecessarily limit the scope of the invention. The exemplary embodiments were chosen and described in order to explain the present invention so that others skilled in the art may practice the invention.

It is claimed:

1. A new and distinct variety of *Loropetalum chinense* plant named 'Shang-white' as illustrated and described herein.

* * * * *